United States Patent [19]

Wang et al.

[11] Patent Number: 5,686,423
[45] Date of Patent: Nov. 11, 1997

[54] DI-AND TRI-PEPTIDE MIMETIC COMPOUNDS FOR PARKINSON'S DISEASE

[75] Inventors: Hui-Po Wang; Jia-Shuai Lee; Ming-Cheng Tsai; Hsiao-Hwa Lu; Oliver Yoa-Pu Hu; Wen-Lin Luo, all of Taipei, Taiwan

[73] Assignee: Department of Health, the Executive Yuan, Republic of China, Taipei, Taiwan

[21] Appl. No.: 602,361

[22] Filed: Feb. 16, 1996

[51] Int. Cl.$^6$ .......................... A61K 38/05; A61K 38/06; C07K 5/00

[52] U.S. Cl. ............... 514/18; 514/19; 530/331; 562/444; 562/445

[58] Field of Search ............... 530/331; 514/18–19; 562/444–445

[56] References Cited

PUBLICATIONS

CA: 123(21): 286619P (Wang et al., Chin. Pharm. J. (Taipei) 1995 47(1) 47–58.
CA: 77(7): 62317G (Felix et al., De 2153813 1972).
Nakonteczna et al., Liebiss Ann. Chem. (Oct., 1994) 1055–1058.
Felix et al., J. Med. Chem. vol. 17 No. 4 (1974) 422–426.
Amidon et al., "Absorption of Peptide and Peptidomimetic Drugs", Annu. Rev. Pharmacol. Toxicol. 34;321–341, 1994.
Bai et al., "Structural Specificity of Mucosal–Cell Transport and Metabolism of Peptide Drugs: Implication for Oral Peptide Drug Delivery", Pharmaceutical Research 9:969–978, 1992.
Hu et al., "Use of the Peptide Carrier System to Improve the Intestinal Absorption of L–α–Methyldopa: Carrier Kinetics, Intestinal Permeabilities, . . . ", Pharmaceutical Research 6:66–70, 1989.

*Primary Examiner*—Cecilia J. Tsang
*Assistant Examiner*—Bennett Celsa
*Attorney, Agent, or Firm*—Fish & Richardson P. C.

[57] ABSTRACT

A series of di- and tri-peptide mimetic dopamine prodrugs are synthesized in which D-phenylglycine or D-p-hydroxyphenylglycine is attached as tools for delivery of L-dopa through the intestine via the intestinal dipeptide-mediated carrier transport system. These compounds are found useful as an active ingredient for the treatment of Parkinson's disease.

16 Claims, 2 Drawing Sheets

DI- AND TRI-PEPTIDE MIMETIC COMPOUNDS FOR PARKINSON'S DISEASE

BACKGROUND OF THE INVENTION

L-Dopa [2-amino-3-(3,4-dihydroxyphenyl)propanoic acid] is a prodrug of dopamine. Clinically it is the first drug of choice in management of Parkinson's disease. However, large portion of circulating L-dopa does not penetrate blood brain barrier ($AUC_{CSF}/AUC_{plasma}=12/100$) [Olanow, C. W., Gauger L. L., Cedarbaum J. M. Temporal Relationships between Plasma and Cerebrospinal Fluid Pharmacokinetics of L-Dopa and Clinical Effect in Parkinson Disease. Annals Neuro. 1991, 29, 556–559]. As a consequence, extensive metabolic decarboxylation of L-dopa to dopamine generated peripheral dopamine-related side effects [Barbeau, A. The Use of L-Dopa in Parkinson Disease: A 20 Year follow-up. Trends Pharmacol. Sci. 1981, 297–299]. Moreover, the oral bioavailability of L-dopa is only 33% at up to 1000 mg/day and wide range of inter- and intra-patient variations in rate and extent of absorption were observed. The amphoteric amino acid-like structure may count for the fluctuation of L-dopa in oral bioavailability.

SUMMARY OF THE INVENTION

In this invention, we designed and prepared a series of di- and tri-peptide derivatives of L-dopa as dopamine prodrugs not only for the purpose of improving the fluctuating bioavailability of L-dopa but also for increasing the cerebral bioavailability of dopamine by targeting the prodrugs through blood brain barrier (B.B.B.) to CNS via the small peptide, transport mechanisms.

A series of di- or tri-peptide derivatives of L-dopa [2-amino-3-(3,4-dihydroxyphenyl)propanoic acid] having the following formula are synthesized in the present invention:

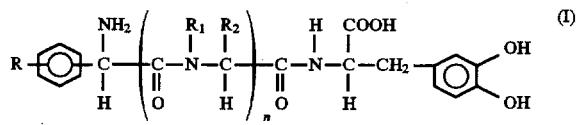

wherein n is 0 or 1;

R is hydrogen or hydroxyl, preferably R is hydroxyl;

$R_1$ is hydrogen; and $R_2$ is hydrogen, alkyl of from one to four carbon atoms, alkyl of from one to four carbon atoms substituted with one —OH, —SH, —$SCH_3$, —$NH_2$, —NHC(=NH)$NH_2$, —COOH, phenyl, hydroxyphenyl, indolyl or imidazolyl group, alkyl from one to four carbon atoms substituted with one carboalkoxyl group of from one to six carbon atoms, preferably $R_2$ is hydrogen, methyl or hydroxymethyl; or $R_1$ and $R_2$ together is trimethylene.

Preferably, $R_1$ and $R_2$ of the di- or tri-peptide derivative of 2-amino-3-(3,4-dihydroxyphenyl-)propanoic acid of the formula (I) together is trimethylene.

Di-peptide derivatives of L-dopa [2-amino-3-(3,4-dihydroxyphenyl)propanoic acid] having the following formula are also synthesized by the present inventors:

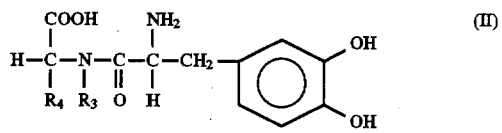

wherein $R_3$ is hydrogen; and $R_4$ is phenyl or hydroxyphenyl; or $R_3$ and $R_4$ together is trimethylene.

A pharmaceutical composition for the treatment of Parkinson's disease is disclosed in the present invention, which comprises a therapeutically effective amount of a di- or tri-peptide derivative of 2-amino-3-(3,4-dihydroxyphenyl)propanoic acid of the formula (I) as defined above or a pharmaceutically acceptable salt thereof, as an active ingredient, in combination with a pharmaceutically acceptable carrier or diluent for the active ingredient.

Another pharmaceutical composition for the treatment of Parkinson's disease is also disclosed in the present invention, which comprises a therapeutically effective amount of a di-peptide derivative of 2-amino-3-(3,4-dihydroxyphenyl)propanoic acid of the formula (II) as defined above or a pharmaceutically acceptable salt thereof, as an active ingredient, in combination with a pharmaceutically acceptable carrier or diluent for the active ingredient.

Oral absorption of the di- and tri-peptide derivatives of the formulas (I) and (II) are investigated in the present invention. These derivatives show high oral bioavailability with some compounds having the plasma concentration 60–100 fold higher than that of L-dopa. The data indicate that these prodrugs are better absorbed in the intestine than the parent drug and D-phenylglycine or D-p-hydroxyphenylglycine are proved to be an efficient tool in delivering the parent drug through the intestine.

DETAILED DESCRIPTION OF THE INVENTION

Figure 1A:
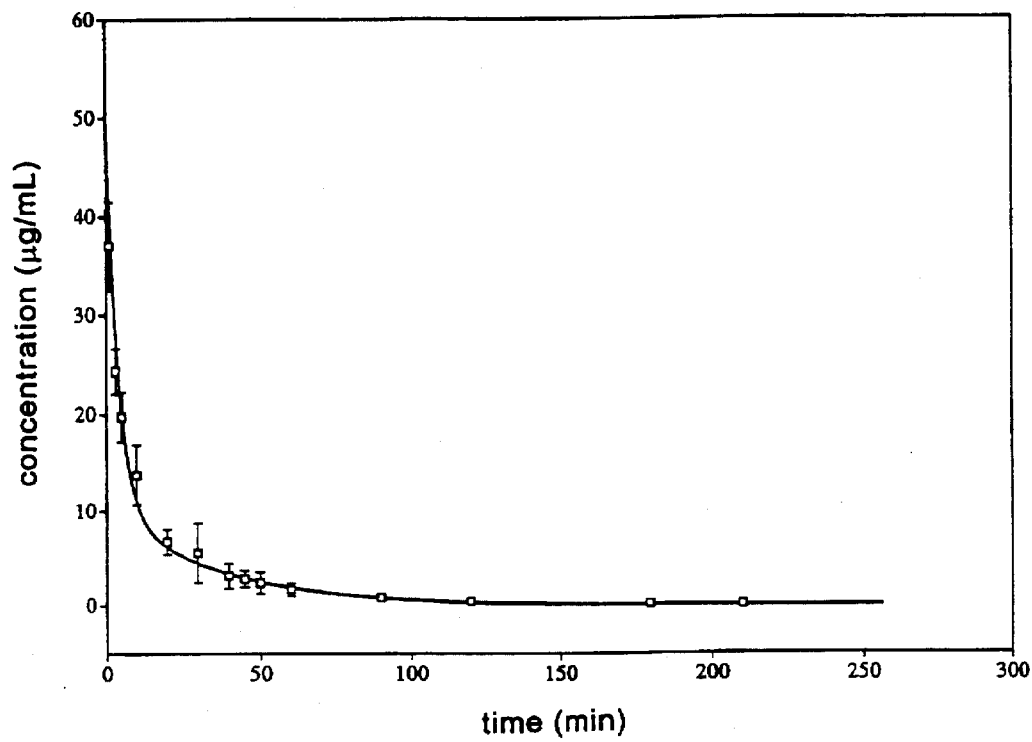
FIG. 1(a) shows the plasma concentration time curve of compound 1a after intra-artery injection.

Prodrugs, structurally modified from existing drugs so as to improve the pharmacokinetic properties, has been the trend of new drug development. Application of the concept of chemical delivery system in prodrug design is especially important. Studies have revealed that certain dipeptide-mediated carrier system was responsible for intestinal absorption of amino-β-lactams [Okano, T., Inui, K., Maegawa, H., Takano, M., Hori, R. $H^+$ coupled uphill transport of aminocephalosporins via the dipeptide transport system in rabbit intestinal brush-border membranes. J. Biol. Chem. 1986, 261, 14130–14134; Dantzig, A. H., Bergin, L. Carrier-mediate uptake of cephalexin in human intestinal cells. Biochim. Biophys. Res. Commun. 1988, 155, 1082–1087; Inui, K., Okano, T., Maegawa, H., Karo, M., Takano, M., Hod, R. H⁺ coupled transport of p.o. cephalosporins via dipeptide carriers in rabbit intestinal brush-border membranes: difference of transport characteristics between cefixime and cephradine. *J. Pharmacol. Exp. Ther.* 1988, 247, 235–247; Wang, H. P., Bair, C. H., Huang, J. D. Uptake of cefadroxil derivatives into rat intestinal brush-border membrane vesicles. *J. Pharm. Pharmacol.* 1992, 44, 1027–1029]. These amino-β-lactams are tripeptide mimetics and most of them include nonessential amino acid moieties, D-phenylglycine or D-p-hydroxyphenylglycine. Since the intestinal dipeptide-mediated carrier transport systems showed broad specificity with less structural requirement on substrates [Bai, J. P. F., Amidon, G. L. Structural specificity of mucosal-cell transport and metabolism of peptide drugs: implication for oral peptide drug delivery. *Pharm. Res.* 1992, 9, 969–978], we used some D-phenylglycine- or D-p-hydroxyphenylglycine-containing dipeptides as tools for delivering oral drugs with poor bioavailability. Preliminary in vitro absorption studies on rat intestinal brush-border membrane vesicles revealed that these dipeptides have high affinity to the intestinal protein responsible for carrier-mediated transport systems [1. Wang, H. P.; Lu, H. H.; Lee, J. S., Cheng, C. Y.; Mah, J. R.; Hsu, W. L.; Yen, C. F.; C. J.; Kuo. H. S.. Intestinal Absorption Studies on Peptido Mimetic Prodrugs of α-Methyldopa. *J. Pharm. Pharmacol.* 1996, 48 (2), in press. 2. Wang, H. P.; Huang, J. D.; Cheng, C. Y.; Bair, C. H.; Lee, J. S.; Chee, P. J. Studies on the Uptake of Dipeptides in Brush Border Membrane Vesicle from Rat Intestine, *Chin. Pharm. J.* 1995, 47, 23–35]. The results are encouraging. We further applied these amino acids and their dipeptide derivatives in preparing a series of L-dopa prodrugs. The intestinal absorption was evaluated by means of in situ single-pass rat jejunal perfusion experiments and by in vivo bioavailability studies on rabbits. Anti-Parkinsonism effect was evaluated by measuring the rotational behavior change in nigrostriatal-lesioned rats elicited by (+)-methamphetamine. The peripheral dopamine-related side effects was measured on the resting contraction of pulmonary artery and vas deference of male guinea pigs.

Chemistry

Dipeptide mimetic prodrugs of dopamine, compounds 1a–1b for example, were prepared by coupling respective N terminal-protected amino acids with L-dopa benzyl ester in the presence of dicyclohexyl carbodiimide (DCC) and N-hydroxybenzotriazole (HOBt), followed by deprotection (Scheme 1). Dipeptide mimetic prodrugs of dopamine with opposite amino acid sequence, such as 1c and 1d, were prepared similarly by coupling N(Boc)-L-dopa with respective amino acid benzyl ester (Scheme 2). The tripeptide mimetic prodrugs, 2a–2d for example, were prepared by coupling N terminal-protected dipeptides with L-dopa benzyl ester, followed by deprotection (Scheme 3).

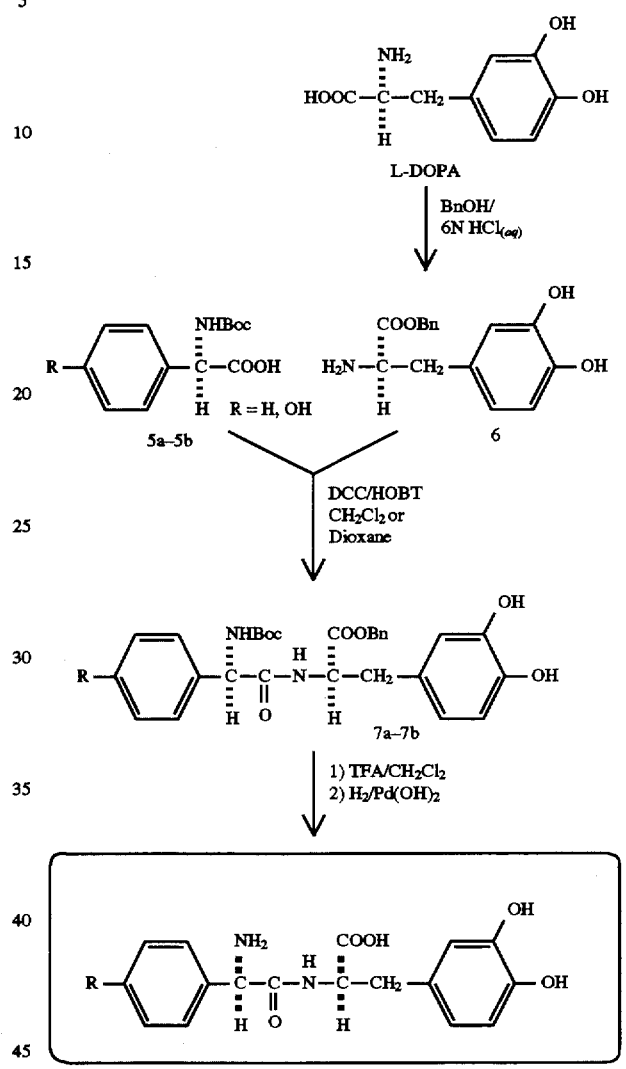

Scheme 2
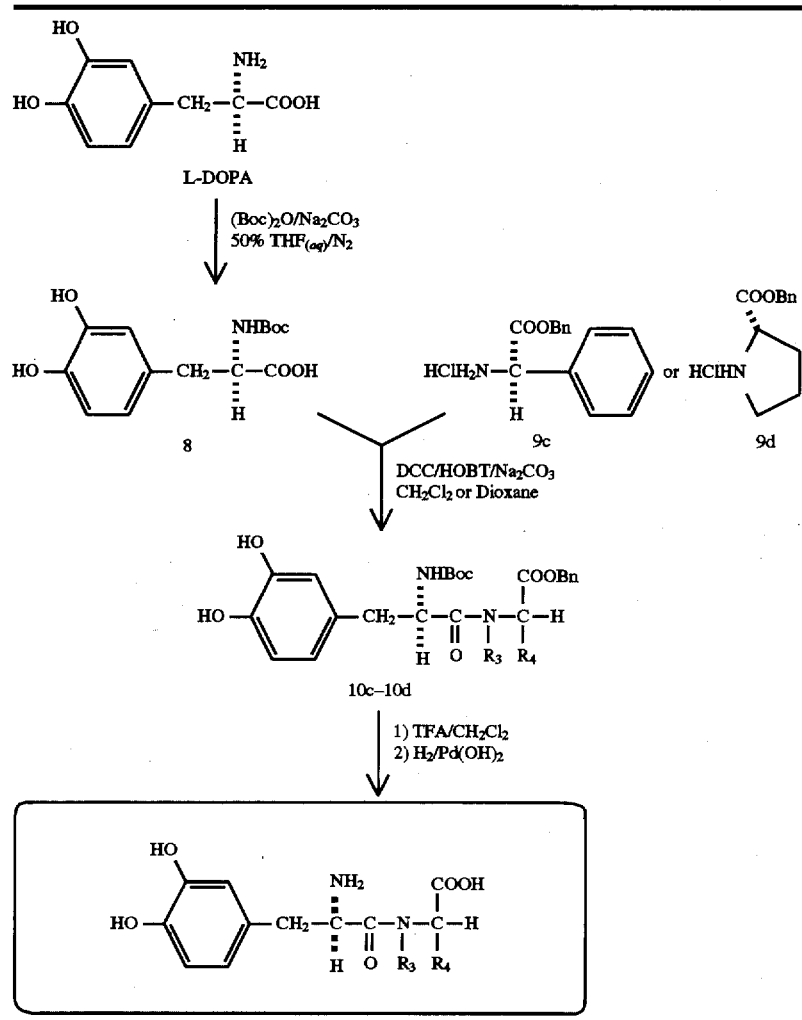
| Compd | $R_3$ | $R_4$ | dipeptide sequence |
|---|---|---|---|
| 1c | H | Ph | L—H-Dopa-D—C(Ph)Gly—OH |
| 1d | —$CH_2$—$CH_2$—$CH_2$— | | L—H-Dopa-L—Pro—OH |
Scheme 3
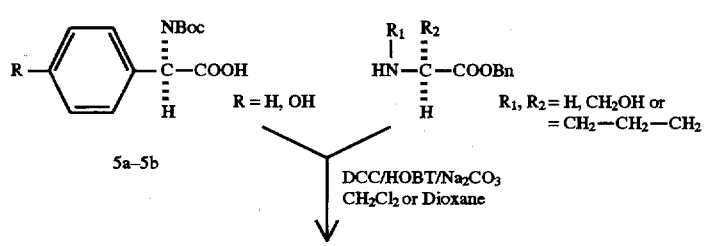

Scheme 3

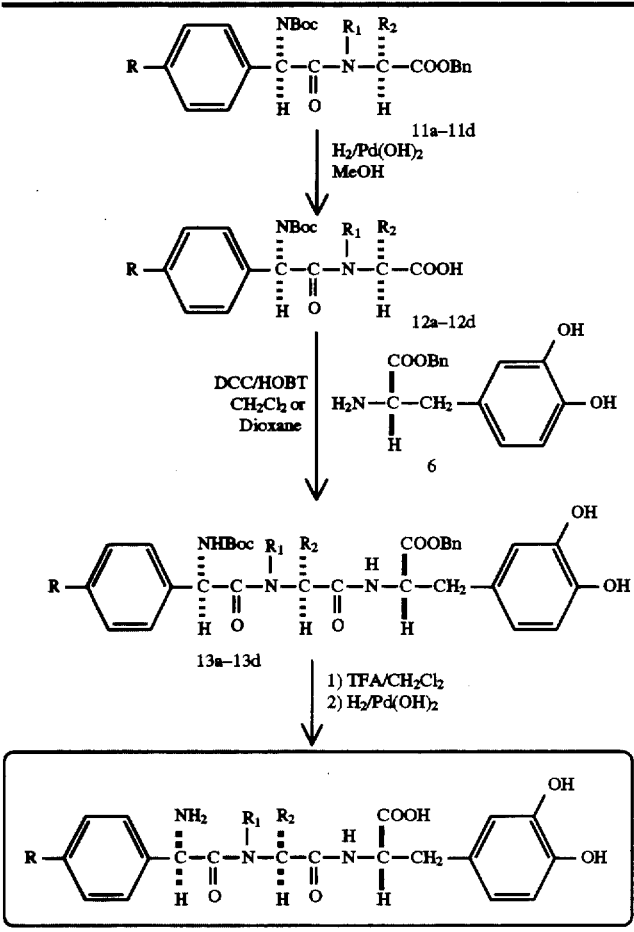

| Compd | R  | R₁              | R₂       | tripeptide sequence |
|-------|----|-----------------|----------|---------------------|
| 2a    | H  | H               | CH₂OH    | D—H—C(Ph)Gly—L—Ser—L-Dopa-Ol |
| 2b    | OH | H               | CH₂OH    | D—H—C(p-HOPh)Gly—L—Ser—L-Dopa-C |
| 2c    | H  | —CH₂—CH₂—CH₂—   |          | D—H—C(Ph)Gly—L—Pro—L-Dopa-Ol |
| 2d    | OH | —CH₂—CH₂—CH₂—   |          | D—H—C(p-HOPh)Gly—L—Pro—L-Dopa-C |

Intestinal Absorption

Upon incubation in a rat intestinal mucosa suspension at 37° C. for 2 minutes, 81% of the dipeptide L-glycine-L-phenylalanine comprising essential amino acids was rapidly degraded. However, the peptide mimetic prodrugs were stable in the same preparation. As depicted by the stability study on D-phenylglycine-L-proline-L-dopa (2d), 94±0.03% (n=2) of the compound remained intact after 90 minutes of incubation. The peptide mimetic compounds comprising nonessential amino acids demonstrated sufficient stability toward enzymatic degradation prior to the absorption.

The intestinal absorption of the prodrugs was then investigated by measuring the plasma concentration in rats upon in situ single-pass rat jejunal perfusion, and by determining the fraction of absorption in rabbits with data obtained from single-dose intra-artery injection and oral administration. As shown in Table 1, all the prodrugs show higher plasma concentration than L-dopa with compounds 1a, 1c, 2b and 2c having the concentration 60–100 fold higher than that of L-dopa. The data indicate that these prodrugs are better absorbed in the intestine than the parent drug.

Figure 1B:
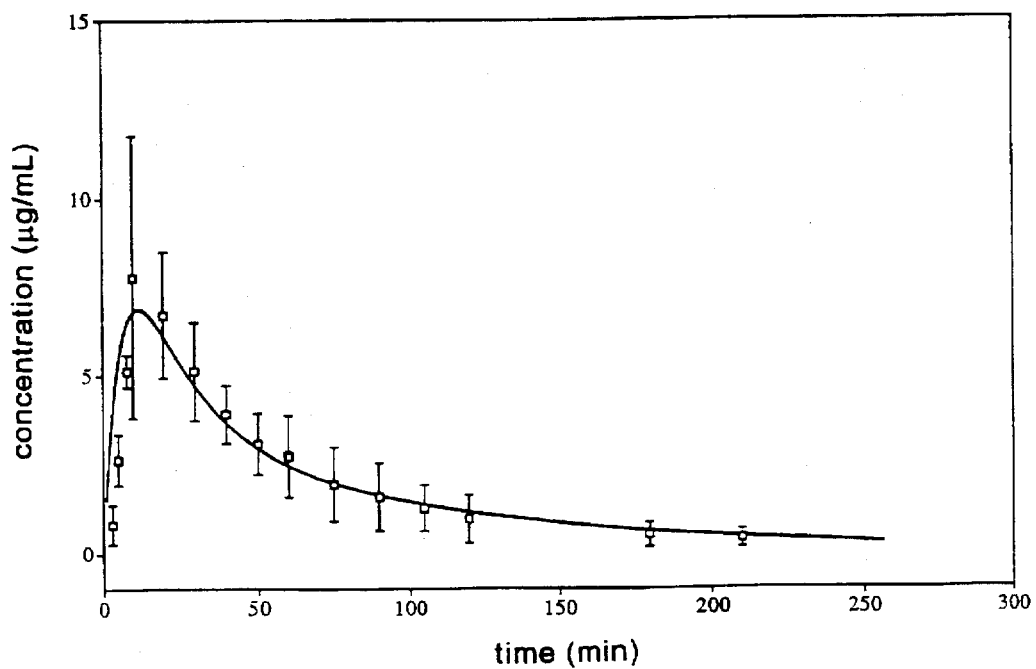
FIG. 1(b) shows the plasma concentration time curve of compound 1a after oral administration.

Prodrug 1a was subjected to single dose oral and intra-artery (i.a.) administrations on 6 fasted New Zealand white rabbits for oral bioavailability study. Plasma concentration time curves of compound 1a after 10 mg/Kg (equivalent to 5.97 mg/Kg of L-dopa) i.a. and oral dose are shown in FIGS. 1(a) and 1(b) respectively. Pharmacokinetic parameters are summarized in Table 2. Oral Absorption of compound 1a is rapid with a $t_{1/2}$ of 61±23 min and bioavailability of 76 (±24)%. The results indicate that D-phenylglycine is an efficient tool in delivering L-dope through the intestine.

TABLE 1

Summary of in situ single-pass rat jejunal perfusion studies.

| compound[a] | sequence | No. of experiment | plasma conc. mg/mL (mean ± s.e.m) |
|---|---|---|---|
| 1a | D-phenylglycine-L-dopa | 4 | 64.65 ± 5.45 |
| 1b | D-p-hydroxyphenyl-glycine-L-dopa | 4 | 0.60 ± 0.01 |
| 1c | L-dopa-D-phenylglycine | 4 | 104.00 ± 12.98 |
| 2a | D-Phenylglycine-L-serine-L-dopa | 6 | 8.49 ± 1.36 |
| 2b | D-p-hydroxyphenyl-glycine-L-serine-L-dopa | 4 | 62.1 ± 3.53 |
| 2c | D-phenylglycine-L-proline-L-dopa | 4 | 84.66 ± 6.00 |
| 2d | D-p-hydroxyphenyl-glycine-L-proline-L-dopa | 6 | 4.37 ± 0.45 |
| L-dopa | — | 3 | 1.24[b] |

[a]The concentration of the perfusate for each compound was 0.1 mM.
[b]Plasma concentration was detected in one rat while was undetectable in the other two.

TABLE 2

Pharmacokinetic parameters of compound 1a after oral and intra-artery (i.a.) administration.[a]

| compound[b] | $C_{max}$ (μg/mL) | $t_{max}$ (min) | AUC (μg. min/mL) | $t_{1/2}$ (min) | fraction of absorption |
|---|---|---|---|---|---|
| 1a oral | 8.29 ± 3.39 | 13 ± 5 | 484.24 ± 91.14 | 61 ± 23 | 76 ± 24% |
| 1a i.a. | 43.22 ± 8.41 |  | 563.05 ± 107.06 | 51 ± 26 |  |

[a]Data presented are mean ± s.e.m. of six rabbits.
[b]Dose of prodrug 1a is 10 mg/Kg.

Pharmacology

Anti-Parkinsonism effect was determine by virtue of measuring the change in rotational behavior of 6-hydroxydopamine-lesioned male Wistar rats [Hudson J. L.; Levin. D. R.; Hoffer, B. J. A Sixteen-Channel Automated Rotometer System For Reliable Measurement of Turning Behavior in 6-Hydroxydopamine Lesioned and Transplanted Rats. Cell Transplantation 1993, 2, 507–514; Hudson J. L, Van Horne C. G.; Stromberg I.; Brock. S.; Clayton, J.; Masserano, J.; Hoffer, B. J.; Gerhardt, G. A. Correlation of Apomorphine and Amphetamine Induced Turning With Nigrostriatal Dopamine Content in Unilateral 6-Hydroxydopamine Lesioned Rats. Brain Res. 1993, 626, 167–174]. Our previous work revealed that animals with unilateral lesion induced by 6-hydroxydopamine rotating more than 300 turns/h in rotometers in response to 0.05 mg/kg s.c. treatment of (+)-methamphetamine had more than 90% probability of possessing a greater than 90% depletion of dopamine in lesioned striatum. Thus, in the present invention, only unilateral 6-hydroxydopamine-induced lesion animals showing greater than 300 turns/h of rotation after methamphetamine treatment were chosen for the experiment. This rotational behavior was persistent and reproducible for at least 6 months after the lesion. In this invention, L-dopa and compound 2d were administered i.p. to the test group of animals 1–2 hours prior to (+)-methamphetamine (0.40 mg/kg, s.c.) treatment. As indicated in Table 3, compound 2d significantly prohibited the (+)-methamphetamine-induced rotation of the unilateral-lesioned rats. The activity is slightly higher than that of L-dopa.

TABLE 3

Effect of L-dopa and compound 2d on rotational behavior of nigrastriatal lesioned rats elicited by (+)-methamphetamine.

| compound | dose (mg/kg) | time (h)[a] | no. of experiment | rotation (turns/h) |
|---|---|---|---|---|
| control saline | — | — | 19 | 552 ± 47 |
| L-Dopa | 4.2 | 1 | 2 | 287 ± 86 |
| 2d | 9.6 | 1 | 6 | 223 ± 95 |
| 2d | 9.6 | 2 | 6 | 247 ± 67 |

[a]Time of (+)-methamphetamine injection after treatment with L-dopa or compound 2d.

Figure 2:
FIG. 2 shows the effects of dopamine (curve A) and compound 2d (curve B) on the resting tension of the pulmonary artery, in which dopamine (1 mg/ml) and compound 2d (1 mg/ml) were administered, respectively for one minute at the points indicated by arrows.
Figure 3:
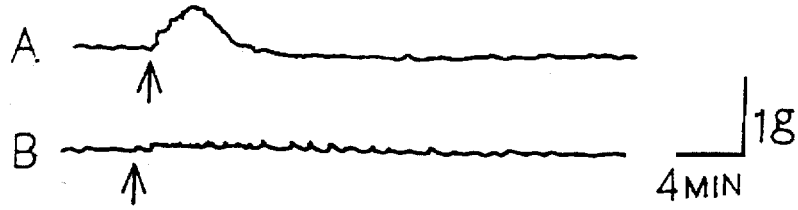
FIG. 3 shows the effects of dopamine (curve A) and compound 2d (curve B) on the resting tension of the vas deferences of guinea pig ileum, in which dopamine (1 mg/ml) and compound 2d (1 mg/ml) were applied respectively for one minute at the points indicated by arrows.

To determine the dopamine-like side effect on pheripheral system, comparative effect of compound 2d and dopamine on the resting tension of the pulmonary artery and the vas deferences of male guinea pigs (250–350 g) was determined according to established procedures. Each experiment was repeated at least three times. The mean responses before and after drug treatment were compared by means of Student's t test, with p<0.05, indicating significance. The contractile force of both pulmonary artery and vas deferences was elicited after continuous perfusion of dopamine (1 mg/mL) for one min. However, no significant contraction was observed after continuous perfusion of compound 2d (1 mg/mL) for 1 min as shown by the curves A in FIGS. 2 and 3. This compound apparently had little effect on the smooth muscles tested.

In this invention, we designed and synthesized a series of di- and tri-peptide mimetic dopamine prodrugs in which nonessential amino acids D-phenylglycine or D-p-hydroxyphenylglycine was attached either directly or via an essential amino acid to L-dopa as tools for oral delivery. The result of intestinal absorption suggested that these compounds are better absorbed than L-dopa and might be feasible to be formulated as oral prodrug of dopamine. Study for anti-Parkinsonism effect was conducted on nigrastriatal lesioned rats. Some of the compounds demonstrated significant activity. The results suggested that the dipeptide or the tripeptide type of compounds are potential Anti-Parkinsonism agent. Without peripheral dopamine-like side effects, the compounds may be beneficial for patients of Parkinson disease with hypertension.

DETAILED DESCRIPTION OF EXPERIMENT

Materials

Potassium chloride, sodium chloride, sodium hydroxide, ascorbic acid, sodium taurocholate, urethane, mannitol, trifluoracetic acid (TFA), sodium 1-pentanesulfonate and sodium dodecyl sulfate were from Sigma, E. Merck, Aldrich and Wako Companies. All chemicals were of analytical grade and used as received. HPLC grade acetonitrile, tetrahydrofuran (THF) and methanol were purchased from Alpus Chemical Company. Melting points (Büchi 510 capillary melting point apparatus) were uncorrected. Spectra were recorded on Perkin-Elmer 1760 FT-IR spectrophotometer, and Bruker 80 or 300 MHz NMR spectrometer. Chemical shifts are recorded in parts per million relative to internal tetramethylsilane. Mass and high-resolution mass (HRMS) were measured on Finnigan MAT 4510 and JEOL JNS-D300 spectrometer respectively. Elemental analyses were performed on Perkin-Elmer 240C elemental analyzer. Male Wistar rats weighing 200–350 g were used to prepare the intestinal mucosa suspension and in perfusion studies. The same species of rats weighing 150–175 grams were used in rotational behavior and in smooth muscle contraction experiments. H—C(p-HO-Ph)Gly-OH=D-p-hydroxyphenylglycine; L-Pro=L-proline; L-Dopa=L-dopa; DCC=dicyclohexylcarbodiimide; HOBt=1-hydroxybenzotriazole.

General Synthetic Procedures

A. Boc Protection

A solution of $(Boc)_2O$, $Na_2CO_3$ and the amine compound in molar ratios 1:2:1 in $THF/H_2O$ solvent system (1:1 v/v) was stirred at room temperature for 24 h. THF was removed in vacuo. The aqueous residue was acidified with $KHSO_4$ to pH 1–2 and extracted with EtOAc three times. The combined EtOAc solution was dried over $MgSO_4$ and filtered. The filtrate was concentrated in vacuo and the residue was recrystallized to give the desired product.

B. Peptide Coupling Using DCC and HOBt

A solution of the N-protected acid component, the C-protected amine component, HOBt and DCC in molar ratio 1:1:1:1.1 in dioxane was stirred at room temperature until the reaction was complete. The solid precipitate was filtered off. The filtrate was concentrated in vacuo. The residue was partitioned between EtOAc and aqueous $KHSO_4$ solution (5%). The combined EtOAc solution was dried over $MgSO_4$ and filtered. The filtrate was concentrated in vacuo. The solid residue was chromatographed when necessary to yield the coupled peptide product.

C. Boc Deprotection

The solution of the Boc-protected amine in trifluoroacetic acid and $CH_2Cl_2$ (1:1 v/v) was stirred at room temperature. The volatile components were removed in vacuo and n-hexane was added to the residue to facilitate precipitation. Most of Boc-deprotected intermediates were used directly without further purification.

D. Hydrogenolysis of Benzyl esters

A solution of the peptide benzyl ester or the N—Cbz-protected amines in MeOH was subjected to hydrogenolysis in the presence of $Pd(OH)_2/C$ (20% Pd) under hydrogen (14.7 psi). When the reaction was judged complete, the catalyst was removed on filtration and the solvent was evaporated to give the desired product.

D—N(Boc)-C(Ph)Gly-L-Dopa-OBn

This compound was synthesized from D—N(Boc)-C(Ph)Gly-OH and L-dopa-OBn via general procedure B (yield 88%): mp 71°–72° C.

D—H—C(Ph)Gly-L-Dopa-OH (1a)

This compound was synthesized from D—N(Boc)-C(Ph)Gly-L-Dopa-OBn via general procedures C and D (yield 88%): mp 76°–78° C.; HRMS (FAB⁻) for $C_{17}H_{17}N_2O_5$ m/z: Calcd 329.1137 (M—H)⁻; Found 329.1134.

L—N(Boc)-Dopa-D—C(Ph)Gly-OBn

This compound was synthesized from L—N(Boc)-Dopa and D-phenylglycine benzyl ester via general procedure B (yield 65%): mp 69°–70° C.

L—H-Dopa-D—C(Ph)Gly-OH (1c)

This compound was synthesized from L—N(Boc)-Dopa-D—C(Ph)Gly-OBn via general procedures C and D (yield 59%): mp 216° C. decomposed; HRMS (FAB⁻) for $C_{17}H_{17}N_2O_5$ m/z: Calcd 329.1137 (M—H)⁻; Found 329.1134.

L—N(Boc)-Dopa-L-Pro-OBn

This compound was synthesized from L—N(Boc)-Dopa and L-proline benzyl ester via general procedure B (yield 46%): mp 91°–93° C.

L-H-Dopa-L-Pro-OH (1d)

This compound was synthesized from L—N(Boc)-Dopa-L-Pro-OBn via general procedures C and D (yield 31%): mp 63°–64° C.; HRMS (FAB⁻) for $C_{14}H_{17}N_2O_5$ m/z: Calcd 293.1137 (M—H)⁻; Found 293.1129.

D—N(Boc)-C(p-HOPh)Gly-L-Pro-OBn

This compound was obtained as white powders by coupling D—N(Boc)-p-hydroxyphenylglycine and L-proline benzyl ester via general procedure B (yield 77%); mp 204° C.; IR (KBr) cm⁻¹: 3327 (broad), 2928, 2851, 1742 ($v_{C=O}$), 1719 ($v_{C=O}$), 1645 ($v_{C=O}$), 1627, 1574, 1537, 1518, 1244, 1224, 1185, 1173; ¹H NMR (80 MHz, DMSO-d₆), d 1.33 (s, 9H, t-butyl), 1.50–2.00 (m-$CH_2$—$CH_2$—$CH_2$—N of proline), 5.10 (s, 2H, Ph—$CH_2$—), 5.25 (dd, J=7.27 Hz, 1H, a-H of proline), 5.55 (d, J=8 Hz, 1H, a-H of p-hydroxyphenylglycine), 6.69 & 7.13 (ABq, J=8.38 Hz, 4H, HO—$C_6H_4$—), 7.33 (s, 5H, Ph—H) ppm.

D-Boc-C(p-HO-Ph)Gly-L-Pro-OH

This compound was prepared from D-Boc-C(p-HOPh)Gly-L-Pro-OBn via general procedure D (96.0%) as white powders. It was used directed in the next reaction without further purification.

D-Boc-C(p-HO-Ph)Gly-L-Pro-L-Dopa-OBn

This compound was prepared from D-Boc-C(p-HO-Ph)Gly-L-Pro-OH and L-dopa benzyl ester (yield 72%) as white powder; mp 110°–112° C.; ¹H-NMR (400 MHz, $CDCl_3$): d 1.28 (s, 9H, t-butyl Hs), 1.35–1.70 (m, 4H, —$CH_2$—$CH_2$—$CH_2$—N of proline), 2.60–2.66 (m, 1H, catechol-$CH_2$—), 2.87–2.89 (m, 1H, —$CH_2$—$CH_2$—$CH_2$—N), 3.03–3.05 (m, 1H, catechol-$CH_2$—), 3.36 (m, 1H, —$CH_2$—$CH_2$—$CH_2$—N), 4.41 (d, J=6.0 Hz, 1H, Pro-a-H), 4.69–4.73 (m, 1H, catechol-$CH_2$—CH), 5.03 & 5.09 (ABq, J=12.2 Hz, 2H, Ph—$C_2$—), 5.25 (d, J=7.6 Hz, 1H, HO—Ph—CH), 5.85 (d, J=7.6 Hz, 1H, NHBoc), 6.38 (d, J=8.0 Hz, 1H, catechol H), 6.45 (s, 1H, catechol H), 6.61 (d, J=8.0 Hz, 1H, catechol H), 6.66 (d, J=8.0 Hz, 2H, HO—Ph), 7.04 (d, J=8.0 Hz, 2H, HO—Ph), 7.40 (d, J=8.3 Hz, Pro-CONH) ppm.

D—H—C(p-HO-Ph)Gly-L-Pro-L-Dopa-OH (2d)

This compound was prepared from D-Boc-C(p-HO-Ph)Gly-L-Pro-L-dopa-OBn via general procedures C and D (yield 89%) as white powder; mp 62° C.; ¹H NMR (400 MHz, $D_2O$) d 1.53–1.58 (m, 4H, —$CH_2$—$CH_2$—$CH_2$—N proline), 2.79–2.85 (m, 2H, catechol-$CH_2$—), 2.99 (dd, J=5.9, 14.1 Hz, 1H, catechol-$CH_2$—), 3.38–3.48 (m, 2H, —$CH_2$—$CH_2$—$CH_2$—N), 4.29 (dd, J=3.2, 9.5 Hz, 1H, Pro-a-H), 4.53 (dd, J=5.9, 8.7 Hz, 1H, catechol-$CH_2$—CH), 5.16 (s, 1H, HO—Ph—CH), 6.59 (d, J=8.0 Hz, 1H, catechol H), 6.67 (s, 1H, catechol H), 6.78 (d, J=8.0 Hz, 1H, catechol H), 6.83 (d, J=8.6 Hz, 2H, HO—Ph), 7.20 (d, J=8.6 Hz, 2H, HO—Ph) ppm., HRMS (FAB⁺) for $C_{22}H_{25}N_3O_7$ m/z: Calcd. 444.1771 [M+H]⁺, Found 444.1775.

Studies on Drug Stability—Degradation of Compounds in Intestinal Mucosa Preparation Mucosa suspension was prepared from the intestine of male Wistar rats according to the method of Hu et al. [Pharm. Res. 1989, 6, 66–70]. After abdominal incision the intestinal segment between the beginning of the jejunum and the end of the ileum was removed and everted to let the interior exposed. The mucosal layer was washed with normal saline and then scraped with glass microscope slides. The scraping was collected, diluted 1:9 (v/v) with ice cold isotonic sucrose solution, and ultrasonicated for 200 seconds. The suspension was centrifuged at 2500 rpm for 5 minutes. The supernatant suspension was stored in an ice bath before subjected to degradation study. All the stability studies were conducted right after the mucosa suspension was prepared. One hundred microliter of a methanolic solution of the test compound (1 mg/mL) was diluted with 2.4 mL of an isotonic mannitol buffer solution (pH=6.5) as the stock solution. One hundred microliter of the stock solution was mixed with equal volume of the mucosal suspension. The mixture was incubated in a 37° C. water bath and subjected to sampling at time intervals between zero to 60 minutes. Two hundred microliter of each sampled solution was denatured with MeOH (0.8 mL) and centrifuged at 14000 rpm for 5 minutes. Twenty to one hundred microliters each of the solution was subjected to HPLC assay on a Lichrospher 100 RP-18 column (E. Merck, 5 µm, 250×3.9 mm). Mobile phase for Gly-Phe was 30% $CH_3CN$ and 70% of a 0.1M citrate buffer solution (pH 3.0) containing 0.05% dodecyl sulfate sodium. Samples were eluted at a flow rate of 0.8–1.0 mL/min. Mobile phase for eluting compound 2d was Na dodecyl sulfate (0.05% w/v) in a solvent system of $CH_3CN$:MeOH:ammonium phosphate buffer (0.1M, pH 2.0)=2:2:6 at 1.0 mL/min flow rate.

Intestinal Perfusion

Preparation of Perfusion Solutions

Preparation of perfusion solutions followed the procedure of Lu et al. (J. Pharm. Sci. 1992, 81, 21–25). Perfusion solutions containing 5 mM KCl, 100 mM NaCl, 10 mM MES, 6 mM D-glucose, the testing compound, and 0.02% ascorbic acid as an anti-oxidant, were adjusted to pH 6 with NaOH. Osmolarity, measured by a Wescor 5500 vapor pressure osmometer (Wescor Company, Logan, Utah, U.S.A.), was adjusted to 300±10 mOsm/kg using sodium chloride. Concentration used in the perfusion solutions was 0.1 mM for L-dopa and prodrug 2d. In order to prevent test compounds from oxidation, perfusion solutions were freshly prepared with nitrogen gas bubbled through for 10 min before each perfusion experiment.

In Situ Rat Perfusion

Surgery on rats followed procedures described previously (LU et al., J. Pharm. Sci. 1992, 81, 21–25). Male Wistar Rats were fasted overnight (16–20 h) prior to anesthesia induced by i.m. injection of urethane (1.5 g/kg body weight). Following induction of anesthesia, rats were put on a heating pat to maintain body temperature. A midline longitudinal incision was made and a 5 to 10 cm jejunal segment was cannulated at the distal end to drain perfusates into collecting tubes. The entire surgical area was then covered with parafilm to minimize temperature reduction through evaporation. Tubing and syringes were covered with aluminum foil to retard the oxidation of testing compounds. Perfusion solution was pumped through the jejunal segment at a flow rate of 0.2 mL/min by a syringe pump (Stoelting, KD Scientific, U.S.A.). The jejunal segment was prewashed initially with drug-free buffer for 10 min and then pumped with test solution. Outlet tubing samples were collected every 10 min for 6 collection periods after water and solute transport reached steady-state. After 90 min perfusion, blood sample (1–2 mL) was drawn by cardiac puncture. The blood samples were centrifuged at 3000 rpm for 10 min, the plasma were separated and stored at –20° C. before analysis. The samples were filtered through 0.2 µm membrane filters before injecting into HPLC system.

Bioavailability

Single Dose Intra-Artery Injection

Single intra-artery dose of prodrug 1a or the parent drug was administered in six fasted New Zealand white rabbits, weighting 2.5–3.0 Kg, via ear artery. Blood samples were withdrawn with heparinized syringes from the contralateral artery at time intervals ranged from 1 min to 3.5 h. Freshly drawn heparinized blood was treated with extraction buffer (1 mol of Tris and 20 g of EDTA per liter, pH 8.6) and then extracted with alumina (100 g). The alumina was extracted with acidic buffer and the extract subjected to HPLC analysis.

Single Dose Oral Administration

After wash-out period, the same rabbits were used for single oral dose administration of prodrug 1a with a feeding tube. Blood samples were withdrawn with heparinized syringes from the contralateral artery at time intervals ranged from 3 min to 3.5 h. Freshly drawn heparinized blood was treated similarly as described above before subjected to HPLC analysis on an ion-exchange column using 0.05M NaCl and 0.001M $Na_2EDTA$ in a 0.1M phosphate buffer as the mobile phase. Prodrug 1a and dihydroxybenzylamine, used as an internal standard, were detected with electrochemical detector at 0.750 V of oxidation potential. The maximal plasma concentration ($C_{max}$) and the time to the maximal plasma concentration ($t_{max}$) were determined. The area under the plasma concentration-time profile (AUC) and the terminal half-life ($t_{1/2}$) were calculated. Fraction of absorption was calculated from the pharmacokinetic parameters ($t_{max}$, $C_{max}$, AUC, $t_{1/2}$) obtained from oral and intra-artery administrations.

HPLC Conditions

Assays of L-dopa and test compounds were performed on HPLC consisting an autosampler (Model 717, Waters, Millipore, Milford, Mass., U.S.A.), a solvent delivery pump (Model 600E, Waters), a tunable absorbence detector (Model 484 or 486, Waters), and a PC 486 computer with a chromatography manager software (Millennium 2010, Millipore). L-Dopa from the perfusate was assayed on a Spheri 5RP-18 column (ABI, 5 µm, 250×4.6 mm) at flow rate of 1.0 mL/min with mobile phase comprising MeOH:0.05M $NH_4H_2PO_4$ buffer (pH 4.6) containing 0.02M sodium 1-pentanesulfonate=10:90 (v/v). Prodrug 2d from the perfusate was assayed on a Nucleosil 100-5 C 18, MN column at flow rate of 1.0 mL/min with mobile phase comprising MeOH:0.05M $NH_4H_2PO_4$ buffer containing 0.1% TFA and 0.025% $NH_4OH$=15:85 (v/v). Standards were injected during each assay. Linearity of standard peak area ratios was validated. Numerical computation on data were performed on Statworks and are represented as mean±standard error of mean (s.e.m) for n experiments. Treatment differences were evaluated by t test.

Pharmacology

Effects on rotational behavior

Twenty male Wistar rats weighing 150-175 grams were used. Within a 36 h window, all rats were lesioned by the same investigator using the following procedure. Surgical anesthesia was produced by i.p. injection of 30 mg/kg of sodium pentobarbital. The animals were placed in a stereotaxic frame and the skin over the skull was incised and reflected. Bregma was used as the coordinate origin and a burr-hole was placed in the cranium over the injection site. After a small-needle puncture of the dura and lowering into the brain parenchyma, a solution of 9 mg/4 mL/4 min of 6-hydroxydopamine HCl was injected using a microliter syringe and a 26 gauge dome-tipped needle (AP-4.4 mm, ML 1.3 mm, DV -7.8 mm). The needle was removed after a 1 min delay and the wound was closed. Convalescence occurred in home cages with food and water ad libitum for the duration of the experiment.

On each testing day, the rats were placed into rotometer bowls and were allowed to acclimatize for 10 min. They then received a subcutaneous dose of (+)-methamphetamine (4 mg/kg in vehicle) and were allowed to move within the bowls for at least 60 min, or until they stopped turning. The rats were returned to the home cages after the experiment until next testing session.

The degree of dopamine depletion was evaluated by monthly testing of rotational behavior in a multichannel rotometer system after methamphetamine (4 mg/Kg, s.c.) injection.

Effects on smooth muscles

Male guinea pigs (250-350 g) were stunned and bled. The vas deferences and pulmonary artery were isolated. A piece of the smooth muscle (about 1 mm wide and 7 mm long) was dissected. The isolated part was mounted vertically on an organ bath (1 mL capacity), kept at 35° C. and superfused with a physiological solution at a constant rate of about 2 mL /min (35° C.). The normal physiological solution had the following composition: NaCl (117 mM), KCl (5.9 mM), $CaCl_2$ (2.4 mM), $MgCl_2$ (1.2 mM), D-glucose (11.8 mM) and Tris 20 (pH 7.4 at 35° C.), aerated with 100% oxygen. Drugs tested were perfused for one min and then superfused with normal physiological solution or otherwise indicated. Tension was recorded isometrically by means of a Grass FT03 tranducer connected to a Grass model 7E polygraph or by a Gould UC2 transducer connected to a Gould 2200S recorder. Each experiment was repeated at least three times with different preparations. The mean responses before and after drug treatment were compared by means of student's t test, with $p<0.05$ indicating significance.

What is claimed is:

1. A di- or tri-peptide derivative of 2-amino-3-(3,4-dihydroxyphenyl)propanoic acid having the following formula:

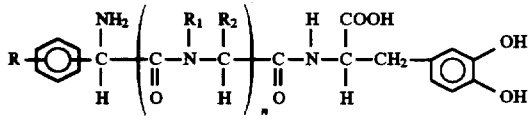

wherein n is 0 or 1;

R is hydrogen or hydroxyl;

$R_1$ is hydrogen; and $R_2$ is hydrogen, alkyl of from one to four carbon atoms, alkyl of from one to four carbon atoms substituted with one —OH, —SH, —$SCH_3$, —$NH_2$, —NHC(=NH)$NH_2$, —COOH, phenyl, hydroxyphenyl, indolyl or imidazolyl group, alkyl from one to four carbon atoms substituted with one carboalkoxyl group of from one to six carbon atoms; or $R_1$ and $R_2$ together is trimethylene.

2. The di- or tri-peptide derivative of 2-amino-3-(3,4-dihydroxyphenyl)propanoic acid according to claim 1, wherein n is 1.

3. The di- or tri-peptide derivative of 2-amino-3-(3,4-dihydroxyphenyl)propanoic acid according to claim 2, wherein $R_2$ is hydrogen, methyl or hydroxymethyl.

4. The di- or tri-peptide derivative of 2-amino-3-(3,4-dihydroxyphenyl)propanoic acid according to claim 2, wherein $R_1$ and $R_2$ together is trimethylene.

5. The di- or tri-peptide derivative of 2-amino-3-(3,4-dihydroxyphenyl)propanoic acid according to claim 1, wherein R is hydroxyl.

6. The di- or tri-peptide derivative of 2-amino-3-(3,4-dihydroxyphenyl)propanoic acid according to claim 4, wherein R is hydroxyl.

7. The di- or tri-peptide derivative of 2-amino-3-(3,4-dihydroxyphenyl)propanoic acid according to claim 1, wherein n is 0.

8. A pharmaceutical composition for the treatment of Parkinson's disease, which comprises a therapeutically effective amount of a di- or tri-peptide derivative of 2-amino-3-(3,4-dihydroxyphenyl)propanoic acid having the following formula or a pharmaceutically acceptable salt thereof, as an active ingredient, in combination with a pharmaceutically acceptable carrier or diluent for the active ingredient:

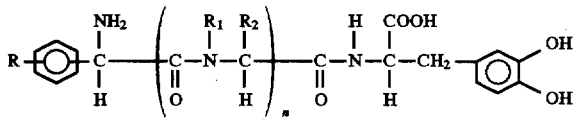

wherein n is 0 or 1;

R is hydrogen or hydroxyl;

$R_1$ is hydrogen; and $R_2$ is hydrogen, alkyl of from one to four carbon atoms, alkyl of from one to four carbon atoms substituted with one —OH, —SH, —$SCH_3$, —$NH_2$, —NHC(=NH)$NH_2$, —COOH, phenyl, hydroxyphenyl, indolyl or imidazolyl group, alkyl from one to four carbon atoms substituted with one carboalkoxyl group of from one to six carbon atoms; or $R_1$ and $R_2$ together is trimethylene.

9. The pharmaceutical composition according to claim 8, wherein n is 1.

10. The pharmaceutical composition according to claim 9, wherein $R_2$ is hydrogen, methyl or hydroxymethyl.

11. The pharmaceutical composition according to claim 9, wherein $R_1$ and $R_2$ together is trimethylene.

12. The pharmaceutical composition according to claim 8, wherein R is hydroxyl.

13. The pharmaceutical composition according to claim 11, wherein R is hydroxyl.

14. The pharmaceutical composition according to claim 8, wherein n is 0.

15. A di-peptide derivative of 2-amino-3-(3,4-dihydroxyphenyl)propanoic acid having the following formula:

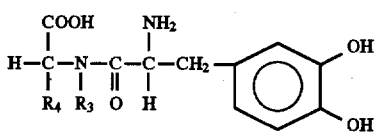

wherein $R_3$ is hydrogen; and $R_4$ is phenyl or hydroxyphenyl; or $R_3$ and $R_4$ together is trimethylene.

16. A pharmaceutical composition for the treatment of Parkinson's disease, which comprises a therapeutically effective amount of a di-peptide derivative of 2-amino-3-(3,4-dihydroxyphenyl)propanoic acid having the following formula or a pharmaceutically acceptable salt thereof, as an active ingredient, in combination with a pharmaceutically acceptable carrier or diluent for the active ingredient:

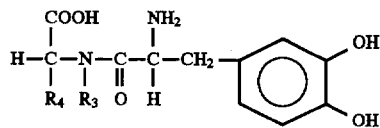

wherein $R_3$ is hydrogen; and $R_4$ is phenyl or hydroxyphenyl; or $R_3$ and $R_4$ together is trimethylene.

* * * * *